United States Patent [19]

Vizi et al.

[11] Patent Number: 4,851,416
[45] Date of Patent: Jul. 25, 1989

[54] BERBAN DERIVATIVES AS $\alpha_2$-ADRENERGIC ANTAGONISTS

[75] Inventors: Szilveszter Vizi; Csaba Szántai; Lajos Szabó; István Tóth; Gabor Kovács; Jenö Marton; László Hársing; György Somogyi; József Gaál, all of Budapest, Hungary

[73] Assignee: Chinoin Gyogyszer es Vegyeszeti Termekek Gyara Rt., Budapest, Hungary

[21] Appl. No.: 867,323

[22] Filed: May 23, 1986

[30] Foreign Application Priority Data

May 24, 1985 [HU] Hungary .................. 1982/85

[51] Int. Cl.[4] ............... A61K 31/47; C07D 455/03
[52] U.S. Cl. .................................. 514/280; 514/284; 546/48; 546/71
[58] Field of Search ................ 546/48, 71; 514/280, 514/284

[56] References Cited

FOREIGN PATENT DOCUMENTS 186854 10/1987 Hungary .

OTHER PUBLICATIONS

Burger, Med. Chem. 2nd ed., pp. 42, 43 (1960).
Szabo et al, Chem. Ber., vol. 4, 109, pp. 1724–1736 (1976).
Toth et al, Jour. Med. Chem., vol. 27, 1411 (1984).
Szabo et al., Chem. Abstracts, vol. 78 (1973), entry 4387q.
Szabo et al, Chem. Abstracts, vol. 78 (1973), entry 4388r.
L. Szabo et al, Chem. Ber., vol. 109, pp. 3390–3403 (1976).
Vizi et al, Journal of Pharmacology & Experimental Therapeutics, vol. 238, pp. 701–706 (1986).
Berbanes: A New Class of Selective $\alpha_2$–Adrenoceptor Antagonists, J. Med. Chem. 1987, 30, 1355–1359. E. Sylvester, Vizi et al, 1987 American Chemical Society. Chem. Ber. 105, pp. 3231–3243 (1972)=Chem. Abstracts (R); Chem. Ber. 105, pp. 3215–3230 (1972)=Chem. Abstracts (S): Chem. Ber 109, pp. 1724–1736 (1976); J. Med. Chem. 27, pp. 1411–1415 (1984); Acta Chim. Acad. Sci., pp. 313–314 (1982), and Drugs of the Future, 10 (10), pp. 841–857 (1985).

Primary Examiner—Anton H. Sutto
Assistant Examiner—Andrew G. Rozycki
Attorney, Agent, or Firm—Herbert Dubno; Jonathan Myers

[57] ABSTRACT

The invention relates to novel racemic or optically active berban derivatives of the formula (I)

wherein
$R^1$ and $R^2$ represent independently from the other a hydroxyl, straight or branched chain alkoxy group 1 to 6 carbon atoms or $R^1$ and $R^2$ together represent a $C_{1-3}$ alkylenedioxy group;
$R^3$ and $R^4$ represent independently from the other hydrogen, straight or branched chain alkyl group, having 1 to 6 carbon atoms and optionally substituted by hydroxyl group, or a $C_{2-6}$ alkoxycarbonyl or cyano group; and
$R^5$ represents hydrogen, straight or branched chain alkyl group having 1 to 6 carbon atoms, $C_{1-7}$ aliphatic or aromatic acyl group or $C_{1-7}$ alkylsulphonyl or arylsulphonyl group, and a salt thereof, to pharmaceutical compositions containing them, to the use as well as to process for preparing the novel compounds. The compounds of the formula (I) are selective $\alpha_2$-adrenergic receptor-blocking substances and thus, they may be used for the treament of depressive illnesses.

9 Claims, No Drawings

BERBAN DERIVATIVES AS $\alpha_2$-ADRENERGIC ANTAGONISTS

The invention relates to novel berban derivatives, to pharmaceutical compositions containing them and, to the use as well as to a process for preparing the novel compounds.

It has been known for a long time that the alkaloids of the Rauwolfia plant family and their analogues with a berban skeleton are biologically active and possess in some cases valuable pharmacological activity.

Antiinflammatory [Acta. Chim. Acad. Sci. Hung. 100, 1 (1979)], prostaglandin-like and prostaglandin antagonist substances [Chem. Ber. 109, 3390 (1976)] as well as antihypertensive compounds [J. Med. Chem., 27, 1411 (1984)] have been found among the above derivatives.

It is known that the nonadrenergic part of the central nervous system plays an important role in the antidepressive action of some compounds [Trends in Pharm. Sci., 1982, 314]. The concentration of norepinephrine (noradrenaline) in the synaptic space is increased under the effect of such compounds. The feed-back inhibition of the norepinephrine release is suspended by the $\alpha_2$-adrenergic antagonists thus, the release of norepinephrine is enhanced. Therefore, a very important therapeutical demand can be satisfied by the $\alpha_2$-antagonists which consists in that they exert a rather weak inhibition on the postsynaptic $\alpha_1$-adrenergic receptors and thus, their selectivity against the $\alpha_2$-receptors is high.

It is the object to prepare therapeutically useful novel compounds which are more selective than the $\alpha_2$-antagonists known so far.

Thus, the invention relates to new racemic or optically active berban derivatives of the formula (I)

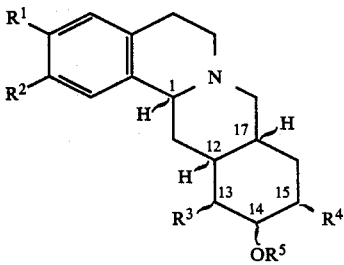

wherein
$R^1$ and $R^2$ represent independently from the other a hydroxyl, straight or branched chain alkoxy group having 1 to 6 carbon atoms or $R^1$ and $R^2$ together represent a $C_{1-3}$ alkylenedioxy group;
$R^3$ and $R^4$ represent independently from the other hydrogen, straight or branched chain alkyl group having 1 to 6 carbon atoms and optionally substituted by hydroxyl group, or a $C_{2-6}$ alkoxycarbonyl or cyano group; and
$R^5$ represents hydrogen, straight or branched chain alkyl group having 1 to 6 carbon atoms, $C_{1-7}$ aliphatic or aromatic acyl group of $C_{1-7}$ alkylsulphonyl group
and a salt thereof.

The meanings of these substituents are always the same in this description therefore and thus will not be repeated hereinafter.

Another aspect of the invention is to provide a process for the preparation of the new compounds of formula (I) and the salts thereof, which comprises reducing a racemic or optically active oxo compound of the formula (II),

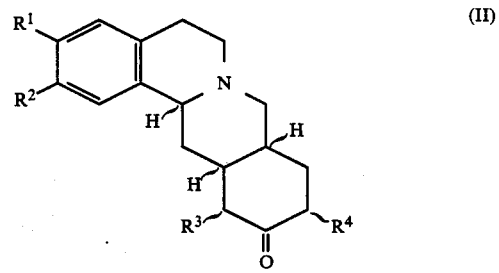

wherein $R^1$, $R^2$, $R^3$ and $R^4$ are the same as above, and optionally resolving, alkylating or acylating the obtained compound of formula (I).

For the preparation of the acid addition salts of the compounds of formula (I), organic and inorganic acids such as tartaric or citric acid and hydrochloric or sulphuric acid may be used.

The reduction of the compounds of the formula (II) can be carried out by using metal hydrides, e.g. sodium borohydride, lithium aluminum hydride or lithium tris(2-butyl)-borohydride or by using hydrogen in the presence of a catalyst, or by the means of sulphur-containing substances, aluminum alkoxides, nascent hydrogen or by using other reagents which are useful to saturate the carbon-oxygen double bond.

In the course of preparing the compounds of formula (I), the nature of the selected reducing agent influences the ratio of the stereoisomers containing the $C_{14}$ hydroxyl group in an equatorial or axial position. For example when the space demand of the metal hydride used for the reduction is enhanced, then the ratio of the isomer containing the $C_{14}$ hydroxyl group in axial position is increased in the product obtained. Using sodium borohydride for the reduction, the isomer containing the $C_{14}$ hydroxyl group in axial position amounts to 80%. When using lithium tris(2-butyl)-borohydride, the product obtained contains nearly exclusively the stereoisomer containing the $C_{14}$ hydroxyl group in axial position. When carrying out the reduction with a system consisting of an alkaline metal and an alcohol, i.e. by using nascent hydrogen, the thermodynamically favorable derivative containing the hydroxyl group in equatorial 14$\alpha$-position is obtained.

The racemic or optically active compounds of formula (II) can be prepared by using methods known from the literature [Chem. Ber., 109, 1724 (1976); and J. Med. Chem. 27, 1411 (1984)].

On investigating the compounds of formula (I), it has been stated that they show a substantially more selective antagonism against the $\alpha_2$-adrenergic receptors as compared to the substances known so far [yohimbine, phentolamine, idazoxan, imiloxan] [see, Drugs of the Future, 10, 841 (1985) and the references cited therein]. The compounds of formula (I) show a very high selectivity concerning the blocking effect on the presynaptic $\alpha_2$- and postsynaptic $\alpha_1$-adrenergic receptors, respectively. The compounds of formula (I) have a very favorable spectrum of activity and do not exert any antagonistic effect on the dopamine, serotonine, histamine or muscarine receptors; in addition, their oral absorption is very good. The substances described in the Examples 3, 25 and 26 are particularly preferably representatives of these compounds.

The above statements are based on the following test-results:

TABLE 1

The action of known α-adrenergic receptor-blocking agents and the compounds of the formula (I) on the $\alpha_2$-receptors of the rat vas deferens (xylazine as agonist) and of the longitudinal smooth muscle preparation of the guinea pig ileum (norepinephrine as agonist)

| Compounds | Rat vas deferens | Longitudinal smooth muscle preparation from guinea pig ileum | Relative activity Vas deferens | Longitudinal smooth muscle preparation of ileum |
|---|---|---|---|---|
| Yohimbine | 7.72 ± 0.11 (4) C | 7.52 ± 0.45 (4) NC | 1.0 | 1.0 |
| Phentolamin | 7.78 ± 0.05 (4) C | 8.82 ± 0.22 | 1.15 | |
| Idazoxan | 8.07 ± 0.04 (4) C | 7.49 ± 0.04 (6) C | 2.23 | 0.79 |
| Imiloxan | 6.84 ± 0.08 (3) C | | 0.13 | |
| Compounds of the formula (I) as hydrochlorides described in Example No. | | | | |
| 1 | 7.18 ± 0.36 (4) C | 7.80 ± 0.22 (6) C | 0.29 | 1.62 |
| 2 | 5.80 ± 0.16 (3) NC | 7.82 ± 0.15 | 0.01 | 1.70 |
| 4 | 7.43 ± 0.11 (3) C | | 0.51 | |
| 5 | 7.99 ± 0.10 (3) C | | 1.86 | |
| 6 | 7.41 ± 0.10 (3) C | | 0.49 | |
| 10 | 6.77 ± 0.06 (5) C | | 0.11 | |
| 11 | 6.42 ± 0.08 (10) C | | 0.05 | |
| 12 | 5.60 ± 0.83 (3) C | 6.69 ± 0.13 | 0.01 | 0.13 |
| 13 | 5.91 ± 0.20 (3) C | | 0.02 | |
| 14 | 6.21 ± 0.11 (3) NC | | 0.03 | |
| As hydrobromide | 5.74 ± 0.11 (8) C | | 0.01 | |
| 17 | 7.39 ± 0.11 (4) C | 6.77 ± 0.22 | 0.47 | 0.15 |
| 25 | 7.63 ± 0.22 (12) C | 7.28 ± 0.17 (4) C | 0.81 | 0.49 |
| 26 | 8.17 ± 0.01 (12) C | 8.26 ± 0.46 (4) C | 2.82 | 4.68 |

METHOD OF THE INVESTIGATION

The tissues were suspended at 37° C. in an organ bath containing 5 ml of Krebs solution. The stimulation was achieved according Field's method by using rectangular impulses (with a frequency of 0.1 Hz, supramaximal potential and an impulse duration of 1 ms). Both the compounds of formula (I) and the reference substances were tested against xylazine (on the rat vas daferens) as well as against epinephrine (on the longitudinal smooth muscle preparation from the guinea pig ileum). The amplitude of the contraction response caused by the stimulation is inhibited on the $\alpha_2$-adrenergic receptors by xylazine or norepinephrine. This effect is abolished by the blocking substances. The pA$_2$ value of the blocking substances was calculated by the means of the negative logarithm of the molar concentration of the blocking substances establishing a dose ratio of 2 [Arunlakshana and Schild: Br. J. Pharmacol., 14, 48 (1959)]. The nature of the competition was similarly studied on the Schild's curve: it was statistically analyzed if the slope of the curve were significantly different from 1. When it is significantly different from 1, then the antagonism is non-competitive (NC); when it is not significantly different from 1, then the antagonism is competitive (C). The ratio of the selective $\alpha_2$-inhibiting effect of the compounds of the formula (I) to that of yohimbine was expressed by the relative activity.

TABLE 2

The action of known α-adrenergic receptor-blocking agents and the compounds of the formula (I) on the $\alpha_1$-receptors of the rat vas deferens and of the pulmonary artery of rabbit against phenylephrine used as agonist

| Compounds | Rat vas deferens pA$_2$ | Pulmonary artery of rabbit pA$_2$ |
|---|---|---|
| Yohimbine | 7.05 ± 0.19 (4) NC | 5.59 ± 0.4 (4) |
| Phentolamine | 8.02 ± 0.25 (4) C | |
| Idazoxan | 6.00 ± 0.16 (4) NC | |
| Imiloxan | 7.28 ± 0.63 (14) NC | |
| Compounds of the formula (I) as hydrochlorides described in Example No. | | |
| 1 | 6.18 ± 0.44 (6) NC | 4.68 ± 0.27 (3) |
| 6 | | 4.61 ± 0.2 (3) |
| 17 | 5.51 ± 0.57 (4) NC | |
| 25 | 4.85 ± 0.15 (4) NC | |
| 26 | 4.95 ± 0.11 (4) NC | |

METHOD OF THE INVESTIGATION

Phenylephrine was used as agonist on the $\alpha_1$-adrenergic receptors whereby both the rat vas deferens and the pulmonary artery of the rabbit were contracted. This concractile effect was inhibited by antagonists. The pA$_2$ value was determined by using the method of Arunlakshana and Schield (1959) cited above. The nature of the competition is also given (NC means non-competitive, C means competitive).

TABLE 3

The action against norepinephrine of known α-adrenergic receptor-blocking agents and the compounds of the formula (I) on the $\alpha_1$-receptors of the pulmonary artery of rabbit

| Compounds | Pulmonary artery of rabbit (pA$_2$) |
|---|---|
| Yohimbine | 5.81 ± 0.37 (4) C |
| Idazoxan | 6.03 ± 0.11 (4) C |
| Compounds of the formula (I) as hydrochlorides described in Example No. | |
| 1 | 6.19 ± 0.07 (4) NC |
| 25 | 4.83 ± 0.52 (4) NC |
| 26 | 5.29 ± 0.20 (8) NC |

METHOD OF THE INVESTIGATION

On the $\alpha_1$-receptors of the pulmonary artery, a contraction is elicited by norepinephrine which is inhibited by antagonists. The pA$_2$ values and the nature of the competition were determined by using the method of Arunlakshana and Schild (1959) cited above (NC means non-competitive; C means competitive).

TABLE 4

Study of the selectivity of known $\alpha$-adrenergic receptor-blocking agents and the compounds of the formula (I) against the $\alpha_2$-receptors on the rat vas deferens

| Compounds | Selectivity $\alpha_1/\alpha_2$ |
|---|---|
| Yohimbine | 4.67 |
| Phentolamine | 0.57 |
| Idazoxan | 117.5 |
| Imiloxan | 0.36 |
| Compounds of the formula (I) as hydrochlorides described in Example No. | |
| 1 | 10.0 |
| 17 | 75.8 |
| 25 | 602 |
| 26 | 1659 |

METHOD OF THE INVESTIGATION

The selectivity values were calculated on the basis of Tables 1 and 2. The pA$_2$ values concerning the $\alpha_1$-receptor of the antagonists were divided by the pA$_2$ values concerning the $\alpha_2$-receptor of the antagonists ($\alpha_1/\alpha_2$). The higher is this ratio, the more selective is the given compound. The low ratio of yohimbine, thought to be a selective antagonist, is surprising.

TABLE 5

Effect of the novel 14$\alpha$-hydroxy-7,8-methylenedioxy-alloberban hydrochloride described in Example 26 and yohimbine on the norepinephrine and dopamine turnover in the cortex and striatum

| Brain part | Catechol-amine | Treatment | NE/DA content (nmole/g) | $K_b$ ($h^{-1}$) | TR$_{CA}$ (nmole/g, $h^{-1}$) | $T_t$ (h) |
|---|---|---|---|---|---|---|
| Frontal Cortex | NE | $\alpha$-MPT | 0.91 ± 0.04 (4) | 0.445 | 0.40 ± 0.01 | 2.24 |
| | | $\alpha$-MPT + * | 0.87 ± 0.05 (4) | 0.740 | 0.64 ± 0.03** | 1.35 |
| | | $\alpha$-MPT + yohimbine | 0.99 ± 0.07 (4) | 0.880 | 0.87 ± 0.06*** | 1.13 |
| Striatum | DA | $\alpha$-MPT | 50.65 ± 3.52 (4) | 0.592 | 29.98 ± 2.08 | 1.68 |
| | | $\alpha$-MPT + * | 48.03 ± 4.66 (4) | 0.776 | 37.27 ± 3.62 | 1.28 |
| | | $\alpha$-MPT + yohimbine | 64.46 ± 6.04 (4) | 0.906 | 58.40 ± 5.47** | 1.10 |

Signs and abbreviations used in the Table 5:
* :14$\alpha$-hydroxy-7,8-methylenedioxy-alloberban hydrochloride
** :p 0.01
NE: norepinephrine
*** :p 0.001
DA: dopamine
$\alpha$-MPT: $\alpha$-methyl-p-tyrosine
TR$_{CA}$: catecholamine turnover

METHOD OF THE INVESTIGATION

Male rats with 100 g of body-weight were intraperitoneally pre-treated (at minute 0) with 320 mg/kg of $\alpha$-methyl-p-tyrosine. The animals of the control group as well as the group treated with the compounds of the formula (I) 4 animals in each group) were killed in the 30th, 60th, 90th and 120th minute, respectively, and the frontal cortex and the striatum were prepared and homogenized in perchloric acid of 0.2 mole/liter concentration. After centrifuging, the norepinephrine content (frontal cortex) or the dopamine content (striatum) of the supernatant, respectively, was determined by using the method of the intense liquid chromatography-electrochemical detection. The fractional rate constant of the catecholamine development ($k_f$) and the catecholamine turnover rate (TR$_{CA}$) in nmole/g×h$^{-1}$ as well as the catecholamine turnover time in hours ($T_t$) were determined by the means of the method of Brodil et al. (1966). The significance level of the difference related to the control group was also determined ( p 0.01; * p 0.001).

The pharmaceutical compositions containing the compounds of the formula (I) may be prepared according to known methods, by using one or more representatives of compounds of the formula (I) together with additives commonly used in the pharmaceutical industry.

The thus-prepared pharmaceutical compositions may be administed orally, parenterally, intravenously or intramuscularly. Preferred forms of the pharmaceutical compositions are the tablets, dragées, capsules, powder mixtures, aqueous suspensions, solutions or injectable solutions. The active ingredient content of the compositions may be varied under wide limits (from 0.005 to 90%).

For the treatment of depression, the compounds of the formula (I) may preferably be used in a daily dose of 5 to 20 mg administered at once or divided in several subdoses. The above dose range is only informative although this may be varied according to the exercise of the physician's discretion.

The invention is illustrated by the following non-limiting Examples.

EXAMPLE 1

Preparation of methyl 14-$\beta$-hydroxy-7,8-methylenedioxy-alloberban-13-carboxylate 10 g (0.26 mole) of sodium borohydride are portionwise added to a solution containing methyl 7,8-methylenedioxy-14-oxoalloberban-13-carboxylate (0.1 mole) in 80 ml of dichloromethane and 200 ml of methanol while stirring and cooling by ice during 1 hour. After ending the addition, the mixture is stirred for additional half hour, then 7 ml of glacial acetic acid are dropped in and evaporated to dryness. The residue is rubbed with water, alkalinized to pH 8 by adding 5% aqueous sodium carbonate solution and extracted with dichloromethane. The dichloromethane phase is evaporated and the residue is recrystallized from methanol to give the title product in a yield of 71%, m.p.: 159°–162° C.

Analysis: Calculated for $C_{20}H_{25}NO_5$ (molecular weight 359.4): C %=66.83; H %=7.01; N %=3.90%.
Found: C %=66.71, H %=7.07, N %=3.71.

IR (KBr): 3500 (OH) 2750–2800 (Bohlmann band), 1700 cm$^{-1}$ (COOCH$_3$).

$^1$H-NMR (CDCl$_3$, $\sigma$); 5.60; 6.62 (2H, s, C$_6$—H, C$_9$—H), 5.85 (2H, s, OCH$_2$O), 4.25 (1H, m, C$_{14}$—H), 3.82 (3H, s, COOCH$_3$).

EXAMPLE 2

Preparation of methyl 14$\beta$-hydroxy-7,8-methylenedioxy-alloberban-15-carboxylate 0.1 mole of 7,8-methylenedioxy-14-oxoalloberban-15-carboxylate is reduced as described in Example 1 to give the title product in a yield of 69%, m.p.: 148°–150° C.

Analysis: Calculated for C$_{20}$H$_{25}$NO$_5$ (molecular weight 359.4): C %=66.83; H %=7.01, N %=3.90.

Found: C %=66.81, N %=7.22, N %=3.72.

IR (KBr): 3460 (OH), 2750–2800 (Bohlmann band), 1700 cm$^{-1}$ $_8$(COOCH$_3$).

$^1$H-NMR (CDCl$_3$, $\sigma$): 6.50, 6.72 (2H, s, C$_6$—H, C$_9$—H), 5.84 (2H, s, OCH$_2$O) 4.25 (1H, m, C$_{14}$—H) 3.68 (3H, s, COOCH$_3$).

EXAMPLE 3

Preparation of 14$\beta$-hydroxy-7,8-methylene-dioxyalloberban 0.1 mole of 7,8-methylenedioxy-14-oxoalloberban is reduced as described in Example 1 and the product obtained is recrystallized from 300 ml of methanol to give the title compound in a yield of 59.8%, m.p.: 172°–175° C. (after recrystallization from ethanol). The hydrochloride melts at 232°–236° C. (after recrystallization from methanol).

Analysis: Calculated for C$_{18}$H$_{23}$NO$_3$ (molecular weight 301.4): C %=71.73, H %=7.68, N %=4.61.

Found: C %=71.77, H %=7.70, N %=4.58.

MS (m/e); 301 (6), 300 (100), 299 (4,2), 284 (6), 282 (1.9), 272 (2.5), 270 (5.6), 260 (0.7), 258 (1), 256 (0.8), 244 (1.2), 242 (3), 240 (1.2), 230 (2.8), 228 (9.6), 226 (2.2), 216 (5.4), 214 (6), 202 (3), 189 (23), 175 (29), 174 (14).

IR (KBr): 3460 (OH) 2750–2800 cm$^{-1}$ (Bohlmann-band).

$^1$H-NMR (CDCl$_3$, $\sigma$): 6.50, 6.72 (2H, s, C$_6$—H, C$_9$—H), 5.85 (2H, s, OCH$_2$O), 4.05 (1H, m, C$_{14}$—H).

The methanolic mother liquid is concentrated and the residue is subjected to flashchromatography on KG-PF$_{254}$ adsorbent by using a 14:1 mixture of benzene/methanol under a pressure of 1.8 atmospheres. A 5% yield of the title product is obtained, further on 14$\alpha$-hydroxy-7,8-methylenedioxyalloberban is obtained in a yield of 14.8%, m.p.: 214°–217° C. (after recrystallization from methanol).

Analysis: Calculated for C$_{18}$H$_{23}$NO$_3$ (molecular weight 301.4): C %=71.73, H %=7.68, N %=4.61.

Found: C %=71.70, H %=7.69, N %=4.52.

MS (m/e): 301 (60), 300 (100), 284 (6.7), 272 (2.2), 260 (0.6), 242 (2.7), 230 (3.0), 228 (12), 216 (7.5), 214 (6.5), 202 (3.1), 190 (14), 189 (29), 176 (13), 175 (33), 174 (18).

IR (KBr): 3450 (OH), 2750–2850 cm$^{-1}$ (Bohlmann-band).

$^1$H-NMR (CDCl$_3$, $\sigma$): 6.52, 6.68 (2H, s, C$_6$—H, C$_9$—H), 5.86 (2H, s, OCH$_2$O), 3.75 (1H, m, C$_{14}$-axH).

EXAMPLE 4

Preparation of (+)—(1R, 12S, 14S, 17R)-14-hydroxy-7,8-methylenedioxyalloberban 0.1 mole of (+)—(1R, 12S, 17R)-7,8-methylenedioxy-14-oxoalloberban is reduced as described in Example 1 to give the title compound in a yield of 61%, [$\alpha$]D$^{20}$=+172° (c=1, dichloromethane), m.p.: 185° C. (after recrystallization from ethanol).

EXAMPLE 5

Preparation of (−)—(1S, 12R, 14R, 17S)-14-hydroxy-7,8-methylenedioxyalloberban 0.1 mole of (−)—(1R, 12S, 17R)-7,8-methylenedioxy-14-oxalloberban is reduced as described in Example 1 to give the title compound in a yield of 57%, m.p.: 185° C. (after recrystallization from ethanol), [$\alpha$]D$^{20}$=−165° (c=1, dichloromethane).

EXAMPLE 6

Preparation of methyl 14$\alpha$-hydroxy-7,8-methylenedioxyberban-13-carboxylate 0.1 mole of methyl 7,8-methylenedioxy-14-oxoberban-13-carboxylate is reduced as described in Example 1 to give the title compound in a yield of 68%, m.p.: 160°–166° C. (after recrystallization from methanol). (This is a mixture of the C$_{13ax}$—COOCH$_3$ and C$_{13eq}$—COOCH$_3$).

Analysis: Calculated for C$_{20}$H$_{25}$NO$_5$ (molecular weight 359.4): C %=66.83, H %=7.01, N %=3.90%.

Found: C %=66.89, H %=7.11, N %=3.90%.

IR (KBr) 3480 (OH), 1720 (C$_{13ax}$—COOCH$_3$) 169 cm$^{-1}$(C$_{13eq}$—COOCH$_3$).

$^1$H-NMR (CDCl$_3$, $\sigma$): 6.55, 6.65 (2H, s, C$_6$—H, C$_9$—H), 4.85 (2H, s, OCH$_2$O), 420 (1H, m, C$_{14}$—H), 3.81, 376 (3H, s, 1/3 COOCH$_3$+⅔ COOCH$_3$)

EXAMPLE 7

Preparation of methyl 14$\alpha$-hydroxy-7,8-methylenedioxyberban-15-carboxylate and methyl 14$\beta$-hydroxy-7,8-methylenedioxyberban-15-carboxylate 0.1 mole of methyl 7,8-methylenedioxy-14-oxoberban-15-carboxylate is reduced as described in Example 1 and the product obtained is separated by using flash chromatography on a Kieselgel-G adsorbent with a 10:1 solvent mixture of chloroform with methanol under a pressure of 1.8 atmospheres. The first title product is obtained in a yield of 21%, m.p.: 185°–187° C. (after recrystallization from methanol).

Analysis: Calculated for C$_{20}$H$_{25}$NO$_5$ (molecular weight 359.4): C %=66.83, H %=7.01, N %=3.90%.

Found: C %=66.22, H %=7.17, N %=3.97%.

IR (KBr): 3350 (OH) 2750–2800 (Bohlmann band), 1710 cm$^{-1}$ (COOCH$_3$).

$^1$H-NMR (CDCl$_3$, $\sigma$): 6.50, 6.70 (2H, s, C$_6$H, C$_9$—H), 5.84 (2H, s, OCH$_2$OH), 4.35 (1H, m, C$_{14}$—H), 3.70 (3H, s, COOCH$_3$).

The second title product is obtained in a yield of 28%, m.p.: 205° C. (after recrystallization from methanol).

Analysis: Calculated for C$_{20}$H$_{25}$NO$_5$ (molecular weight 359.4): C %=66.83, H %=7.01, N %=3.90.

Found: C %=67.10, H %=6.99, N %=3.67.

IR (KBr): 3400 (OH), 2750–2850 (Bohlmann band), 1710 cm$^{-1}$ (COOCH$_3$).

$^1$H-NMR (CDCl$_3$, $\sigma$): 6.52, 6.70 (2H, s, C$_6$—H, C$_9$—H), 5.85 (2H, s, O—CH$_2$O), 3.85 (1H, m, C$_{14}$—H), 3.71 (3H, s, COOCH$_3$).

EXAMPLE 8

Preparation of 14$\beta$-hydroxy-7,8-methylenedioxyberban 0.1 mole of 7,8-methylenedioxy-14-oxoberban is reduced as described in Example 1 to give the title compound in a yield of 70%, m.p.: 217°–219° C. (after recrystallization from methanol).

Analysis: Calculated for $C_{18}H_{23}NO_3$ (molecular weight 301.4): C %=71.73, H %=7.69, N %=7.61.
Found: C %=71.10, H %=7.60, N %=4.57.
IR (KBr): 3350 (OH), 2750–2800 cm$^{-1}$ (Bohlmann band).
$^1$H-NMR (CDCl$_3$, $\sigma$): 6.55, 6.75 (2H, s, C$_6$—H, C$_9$—H), 5.85 (2H, s, OCH$_2$O), 3.65 (1H, m, C$_{14}$—H).

EXAMPLE 9

Preparation of methyl 14β-hydroxy-7,8-methylenedioxy-epialloberban-13-carboxylate 0.1 mole of methyl 7,8-methylenedioxy-14-oxo-epialloberban-13-carboxylate is reduced as described in Example 1 to give the title compound in a yield of 37% (after separation by chromatography), m.p.: 202°–203° C.
Analysis: Calculated for $C_{20}H_{25}NO_5$ (molecular weight 359.4): C %=66.83, H %=7.01, N %=3.90.
Found: C %=66.81, H %=7.22, N %=3.94.
IR (KBr): 3450 (OH), 2750–2850 (Bohlmann band), 1730 cm$^{-1}$ (COOCH$_3$).
$^1$H-NMR (CDCl$_3$, $\sigma$): 6.55, 6.60 (2H, s, C$_6$—H), 5.85 (2H, s, OCH$_2$O), 4.2 (1H, m, C$_{14}$-H), 3.80 (3H, s, COOCH$_3$).

EXAMPLE 10

Preparation of 14α-hydroxy-7,8-methylenedioxy-epialloberban 0.1 mole of 7,8-methylenedioxy-14-oxoepialloberban (0.1 mole) is reduced as described in Example 1 to give the title compound in a yield of 49%. The hydrochloride melts at 212°–216° C. (after recrystallization from methanol).
Analysis: Calculated for $C_{18}H_{24}ClNO_3$ (molecular weight 337.84): C %=63.99, H %=7.16, N %=4.15.
Found: C %=64.24, H %=7.02, N %=4.00.
IR (KBr): 3350 (OH), 2750–2850 (Bohlmann band), 2500–2600 cm$^{-1}$ (salt).
$^1$H-NMR (CDCl$_3$, $\sigma$): 6.50, 6.65 (2H, s, C$_6$—H), 5.85 (OCH$_2$O), 4.10 (1H, m, C$_{14}$—H).

EXAMPLE 11

Preparation of 14β-hydroxy-7,8-diethoxyalloberban 0.1 mole of 7,8-diethoxy-14-oxoalloberban is reduced as described in Example 1 to give the title compound in a yield of 61%, m.p.: 135°–139° C. (after recrystallization from methanol). The hydrochloride melts at 159°–162° C. (after recrystallization from methanol).
Analysis: Calculated for $C_{21}H_{31}NO_3$ (molecular weight 345.47): C %=73.00, H %=9.04, N %=4.06.
Found: C %=72.69, H %=9.15, N %=3.97.
IR (KBr): 3390 (OH), 2750–2800 cm$^{-1}$ (Bohlmann band).
$^1$H-NMR (CDCl$_3$, $\sigma$): 6.70, 6.60 (2H, s, C$_6$—H, C$_9$—H), 4.05 (2H, q, COOCH$_2$CH$_3$), 1.40 (3H, t, COOCH$_2$CH$_3$).

EXAMPLE 12

Preparation of 14β-hydroxy-13hydroxy-methyl-7,8-methylenedioxyalloberban 0.1 mole of 13-hydroxymethyl-7,8-methylenedioxy-14-oxoalloberban dissolved in 300 ml methanol is stirred at room temperature, then 0.52 mole of sodium borohydride are portionwise added to the mixture during about 1 hour. The mixture is stirred at 40° C. for an additional 3 hours, then the pH value is adjusted to neutral by adding 14 ml of glacial acetic acid and the mixture is evaporated to dryness.
The residue is triturated with water and alkalinized to pH 8 by adding 5% aqueous sodium carbonate solution. After filtration, the product is dissolved in 10 ml of methanol, the pH value is acidified to 3 by adding methanolic hydrogen chloride and the thus-obtained product is crystallized to give the hydrochloride of the title compound in a yield of 47%, m.p.: 243°–245° C.
Analysis: Calculated for $C_{19}H_{26}ClNO_4$ (molecular weight 367.86): C %=62.03, H %=7.12, Cl %=9.64, N %=3.81.
Found: C %=62.90, H %=7.27, Cl %=9.02, N %=3.62.
IR (KBr): 3350 (OH), 2750–2800 (Bohlmann band), 1500 cm$^{-1}$ (aromatic).

EXAMPLE 13

Preparation of 14β-hydroxy-15-hydroxy-methyl-7,8-methylenedioxyalloberban 0.1 mole of 15-hydroxymethyl-7,8-methylenedioxy-14-oxoalloberban is reduced as described in Example 12 to give the title compound as the base in a yield of 41.5%, m.p.: 152°–155° C. (after recrystallization from methanol).
Analysis: Calculated for $C_{19}H_{25}NO_4$ (molecular weight 331.4): C %=68.86, H %=7.60, N %=4.23.
Found: C %=68.12, H %=7.87, N %=4.00.
IR (KBr): 3400 (OH), 2750–2850 (Bohlmann band), 1500 cm$^{-1}$ (aromatic).

EXAMPLE 14

Preparation of 14β-hydroxy-13-hydroxymethyl-7,8-methylenedioxyberban 0.1 mole of 13-hydroxymethyl-7,8-methylenedioxy-14-oxoberban is reduced as described in Example 12 to give the hydrochloride of the title compound in a yield of 42%, m.p.: 245°–250° C.
Analysis: Calculated for $C_{19}H_{26}ClNO_4$ (molecular weight 367.86): C %=62.03, H %=7.12, Cl %=9.64, N %=3.81.
Found: C %=61.55, H %=7.70, Cl %=9.01, N %=3.29.
IR (KBr): 3320, 3400 (OH), 2750–2850 (Bohlmann band), 1490 cm$^{-1}$ (aromatic).

EXAMPLE 15

Preparation of 7,8-dihydroxy-14β-hydroxyalloberban 1.0 mmole of 14β-hydroxy-7,8-methylenedioxyalloberban is dissolved in 50 ml of dry dichloromethane, 6 mmoles of boron tribromide are dripped in the solution and stirred for 1 day, then evaporated to dryness. The residue is triturated with acetone, filtered and the precipitate is recrystallized from ethanol to give the hydrobromide of the title compound in a yield of 47%, m.p.: 202° C. (after recrystallization from ethanol).
Analysis: Calculated for $C_{17}H_{24}BrNO_3$ (molecular weight 370.29): C %=55.14, H %=6.53, N %=3.78.
Found: C %=54.81, H %=6.87, N %=3.27.
IR (KBr): 3400 (OH), 2750–2850 (Bohlmann band), 1480 cm$^{-1}$ (aromatic).

EXAMPLE 16

Preparation of 7,8-diethoxy-14-oxoalloberban 10 mmoles of methyl 7,8-diethoxy-14-oxoalloberban-13-carboxylate [J. Med. Chem. 27, 1411 (1984)] and 100 ml of 10% aqueous hydrochloric acid are heated together at 100° C. for 5 hours. After cooling, 100 ml of water are added to the reaction mixture which is then alkalinized to pH 9 by adding 20% aqueous sodium hydroxide solution and extracted with dichloromethane. The organic phase is evaporated and the residue is recrystallized from methanol to give the title compound in a yield of 91%, m.p.: 148°–152° C. (after recrystallization from methanol).

Analysis: Calculated for $C_{21}H_{29}NO_3$ (molecular weight 343.45): C %=73.43, H %=8.51, N %=4.08.
Found: C %=73.10, H %=8.82, N %=3.71.

IR (KBr): 2750–2800 (Bohlmann band), 1700 cm$^{-1}$ (CO).

EXAMPLE 17

Preparation of ethyl 14β-hydroxy-7,8-methylenedioxyalloberban-13-carboxylate 0.1 mole of ethyl 7,8-methylenedioxy-14-oxoalloberban-13-carboxylate is reduced as described in Example 1 to give the title compound in a yield of 81%, m.p.: 149°–162° C. (after recrystallization from ethanol).

Analysis: Calculated for $C_{21}H_{27}NO_5$ (molecular weight 373.44): C %=67.54, H %=7.29, N %=3.75.
Found: C %=67.37, H %=7.31, N %=3.74.

IR (KBr): 3450 (OH), 2750–2800 (Bohlmann band), 1700 cm$^{-1}$ (COOC$_2$H$_5$).

EXAMPLE 18

Preparation of 3β-(β-cyanoethyl)-2β-ethoxycarbonylmethyl-1,2,3,4,6,7-hexahydro-9,10-methylenedioxy-11b(H)-benzo(a)quinolizine A solution containing 2.7 mmoles of 3β-(β-cyanoethyl)-2-ethoxycarbonylmethylene-1,2,3,4,6,7-hexahydro-9,10-methylenedioxy-11b(H)-benzo(a)-quinolizine [Chem. Ber. 109, 1724 (1976)] in 20 ml of methanol is hydrogenated in the presence of 0.5 g of palladium-on-carbon catalyst. After reduction, the catalyst is filtered out, the filtrate is evaporated to dryness and the residue is recrystallized from ethanol to give the title compound in a yield of 0.72 g (72%), m.p.: 97°–97.5° C.

Analysis: Calculated for $C_{21}H_{26}N_2O_4$ (molecular weight 370.44): C %=68.09, H %=7.08, N %=7.56.
Found: C %=68.25, H %=7.07, N %=7.52.

IR (KBr): 2290 (C≡N), 1730 cm$^{-1}$ (C=O).

$^1$H-NMR (CDCl$_3$, σ): 6.68, 6.57 (2H, s, C$_8$—H, C$_{11}$—H), 5.89 (2H, s, OCH$_2$) 4.21 (2H, q, COOCH$_2$CH$_3$), 1.29 (3H, t, COOCH$_2$CH$_3$).

EXAMPLE 19

Preparation of 15-cyano-7,8-methylenedioxy-14-oxo-alloberban 2.7 mmoles of the product prepared as described in Example 18 is dissolved in 10 ml of benzene, 5.35 mmoles of potassium tertiary-butoxide is added and the mixture is boiled under reflux for 30 minutes. Then, the mixture is cooled to room temperature, neutralized by adding acetic acid and evaporated to dryness. The residue is triturated with 2.5% aqueous sodium carbonate solution, filtered and the precipitate is recrystallized from methanol to give the title compound in a yield of 0.7 g (80%), m.p.: 245°–248° C. (after recrystallization from methanol).

Analysis: Calculated for $C_{19}H_{20}N_2O_3$ (molecular weight 324.37): C %=70.42, H %=6.22, N %=8.65.
Found: C %=70.11, H %=6.23, N %=8.52.

IR (KBr): 2750–2800 (Bohlmann band), 2230 (C≡N), 1700 cm$^{-1}$ (C=O).

EXAMPLE 20

Preparation of 15-cyano-14β-hydroxy-7,8-methylenedioxyalloberban 0.01 mole of 15-cyano-7,8-methylenedioxy-14-oxoalloberban is reduced as described in Example 1 to give the title compound in a yield of 87%, m.p.: 225°–226° C. (after recrystallization from methanol).

Analysis: Calculated for $C_{19}H_{22}N_2O_3$ (molecular weight 326.39): C %=69.91, H %=7.80, N %=8.58.
Found: C % =69.79, H %=6.92, N %=8.41.

IR (KBr): 3450 (OH), 2700–2750 (Bohlmann band), 2230 cm$^{-1}$ (C≡N).

EXAMPLE 21

Preparation of 14β-acetoxy-7,8-methylenedioxyalloberban 6.4 mmoles of acetyl chloride is dripped in a solution containing 1 mmole of 14β-hydroxy-7,8-methylenedioxyalloberban in 10 ml of dichloromethane and the thus-obtained solution is set aside for 1 day. Then the mixture is evaporated to dryness, the residue is triturated with 2.5% aqueous sodium carbonate solution, extracted with dichloromethane and the organic phase is evaporated to dryness. The residue is recrystallized from methanol to give the title compound in a yield of 92%, m.p.: 153° C. (after recrystallization from methanol).

Analysis: Calculated for $C_{20}H_{25}NO_4$ (molecular weight 343.41): C %=69.95, H %=7.34, N %=4.08.
Found: C %=69.71, H %=7.34, N %=4.01.

IR (KBr): 2750–2850 (Bohlmann band), 1720 cm$^{-1}$, (CH$_3$CO).

$^1$H-NMR (CDCl$_3$, σ): 6.69, 6.53 (2H, s, C$_6$—H, C$_9$—H), 5.86 (2H, s, OCH$_2$O), 5.03 (1H, m, C$_{14}$—eqH), 1.90 (3H, s, CH$_3$CO).

EXAMPLE 22

Preparation of 14α-acetoxy-7,8-methylenedioxyalloberban 1.0 mmole of 14α-hydroxy-7,8-methylenedioxyalloberban is acylated as described in Example 21 to give the title compound in a yield of 89%, m.p.: 155° C. (after recrystallization from methanol).

Analysis: Calculated for $C_{20}H_{25}NO_4$ (molecular weight 343.41): C %=69.95, H %=7.34, N %=4.08.
Found C %=70.02, H %=7.35, N %=4.05.

IR (KBr): 2750–2850 (Bohlmann band), 1720 cm$^{-1}$, (CH$_3$CO)

$^1$H-NMR (CDCl$_3$, σ): 6.66, 6.52 (2H, s, C$_6$—H, C$_9$—H), 5.84 (2H, s, OCH$_2$O), 4.86 (1H, m, C$_{14}$-axH), 1.96 (3H, s, CH$_3$CO).

EXAMPLE 23

Preparation of 14α-acetoxy-7,8-dimethoxyalloberban 1 mmole of 14α-hydroxy-7,8-dimethoxyalloberban is acylated as described in Example 21 to give the title compound in a yield of 90%, m.p.: 165°–167° C. (after recrystallization from methanol).

Analysis: Calculated for $C_{21}H_{29}NO_4$ (molecular weight 359.45): C %=70.16, H %=8.13, N %=3.90.
Found: C %=70.21, H %=8.09, N %=3.95.

IR (KBr): 2750–2850 (Bohlmann band), 1705 (CH$_3$CO), 1590 cm$^{-1}$ (aromatic).

EXAMPLE 24

Preparation of ethyl 14β-hydroxy-7,8-methylenedioxyalloberban-13-carboxylate A solution containing 1 mmole of methyl 14β-hydroxy-7,8-methylenedioxyalloberban-13-carboxylate and 3 mg of p-toluenesulphonic acid in 5 ml of ethanol is boiled for 5 hours, then evaporated to its one-third volume and the precipitate is filtered. The title compound is obtained in a yield of 59%, m.p.: 142°–146° C. (after recrystallization from ethanol).

Analysis: Calculated for $C_{21}H_{27}NO_5$ (molecular weight 373.4): C %=67.54, H %=7.29, N %=3.75.
Found: C %=67.27, H %=7.32, N %=3.49.
IR (KBr): 3480 (OH), 2750–2800 (Bohlmann band), 1710 cm$^{-1}$ ($COOCH_3$).

EXAMPLE 25

Preparation of 14β-hydroxy-7,8-methylenedioxyalloberban 0.5 g of 7,8-methylenedioxy-14-oxoalloberban (1.67 mmoles) is dissolved in 80 ml of methanol and after adding 0.2 g of Raney nickel catalyst, the mixture is hydrogenated while shaking at atmospheric pressure for 5 hours. After absorption of 40 ml of hydrogen, the catalyst is filtered out, the filtrate is evaporated to dryness and the residue is recrystallized from methanol to give 0.47 g (94%) of the title compound, m.p: 176°–178° C.

EXAMPLE 26

Preparation of 14α-hydroxy-7,8-methylenedioxyalloberban 2 g of sodium metal and 40 ml of abs. xylene are weighed in a 100 ml round-bottom flask. The xylene is heated to boiling by using an infralamp and the molten sodium is dispersed by vigorously shaking the flask. The thus-dispersed sodium is stirred in the xylene by using an electro-magnetic stirrer, cooled to 0° C., then 0.5 g of 7.8-methylenedioxy-14-oxoalloberban (1.67 mmoles) is portionwise added to the suspension. To this solution 5 ml of abs. ethanol are dripped from a dripping funnel during 2 hours, then the mixture is stirred for one additional hour and then evaporated to dryness by using a rotavapor device. The residue is shaken with 10 ml of water and 10 ml of dichloromethane, the dichloromethane phase is dried and evaporated to dryness. After recrystallizing the residue from methanol, the title compound is obtained in a yield of 0.42 g (84%), m.p.: 214°–217° C.

EXAMPLE 27

Preparation of a tablet containing 10 mg of the active ingredient 10 g of 14α-hydroxy-7,8-methylenedioxyalloberban are homogenized with 6 g of talc, 6 g of magnesium stearate, 20 g of polyvinylpyrrolidone, 90 g of maize starch and 160 g of lactose, then 1000 tablets are prepared from this mixture by compression.

We claim:

1. A method of treatment of a mammalian subject susceptible to an α$_2$adrenergic antagonist, which comprises the step of administering to said mammalian subject, an antidepressively effective amount of a compound of the Formula (I)

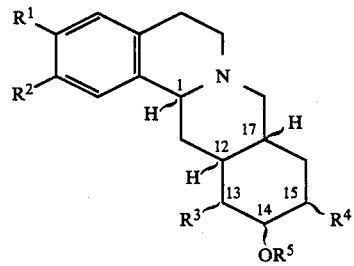

or a pharmaceutically acceptable acid addition salt thereof, wherein
$R^1$ and $R^2$ are the same and are each a hydroxyl, or a straight or branched chain alkoxy group having 1 to 6 carbon atoms or $R^1$ and $R^2$ together represent a methylenedioxy group.
$R^3$ and $R^4$ represent independently from the other hydrogen, straight or branched chain alkyl group having 1 to 6 carbon atoms and optionally substituted by hydroxyl group, or a $C_{2-6}$ alkoxycarbonyl or cyano group, and
$R^5$ represents hydrogen, straight or branched chain alkyl group having 1 to 6 carbon atoms, $C_{1-7}$ alkanoyl, phenylacyl, $C_1$ to $C_7$ alkylsulfonyl or phenylsulfonyl.

2. A compound of the Formula (Ia)

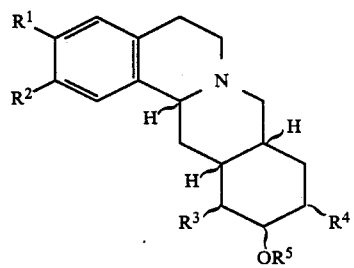

or a pharmaceutically acceptable salt thereof, wherein
$R^1$ and $R^2$ are the same and are each a hydroxy, or a $C_1$ to $C_6$ straight or branched chain alkoxy, or together represent methylenedioxy;
$R^3$ and $R^4$ represent independently from one another hydrogen, straight or branched chain $C_1$ to $C_6$ alkyl unsubstituted or hydroxy-substituted, $C_2$ to $C_6$ alkoxy-carbonyl or cyano, with the proviso that if $R^1$ and $R^2$ at the same time represent methoxy group then $R^3$ or $R^4$ cannot stand for cyano, methoxy-carbonyl or hydroxy substituted methyl group and that if $R^1$ and $R^2$ at the same time represent methoxy groups, then $R^3$ and $R^4$ cannot both stand for hydrogen; and $C_1$ to $C_6$ straight or branched chain alkyl, $C_1$ to $C_7$ alkanoyl, phenylacyl, $C_1$ to $C_7$ alkylsulfonyl, hydrogen or phenylsulfonyl.

3. A compound as defined in claim 2 and selected from the group which consists of:
methyl 14β-hydroxy-7,8-methylenedioxyalloberban-13-carboxylate,
methyl 14β-7,8-methylenedioxyalloberban-15-carboxylate,
14β-hydroxy-7,8-methylenedioxyalloberban,
(+)-(1R, 12S, 14S, 17R)-14-hydroxy-7,8-methylenedioxyalloberban, (−)-(1S, 12R, 14R, 17S)-14-hydroxy-7,8-methylenedioxyalloberban, methyl 14α-hydroxy-7,8-methylenedioxyberban-13-carboxylate, methyl 14α-hydroxy-7,8-methylenedioxyberban-15-carboxylate, methyl 14β-hydroxy-7,8-methylenedioxyberban-15-carboxylate, 14β-hydroxy-7,8-methylenedioxyberban, methyl 14β-hydroxy-7,8-methylenedioxy-epialloberban-13-carboxylate, 14A-hydroxy-7,8-methylenedioxy-epialloberban, 7,8-diethoxy-14β-hydroxyalloberban, 14α-hydroxy-7,8-methylene dioxyalloberban, 14β-hydroxy-13-hydroxymethyl-7,8-methylenedioxyalloberban 14β-hydroxy-15-hydroxymethyl-7,8-methylenedioxyalloberban, 14β-hydroxy-13-hydromethyl-7,8-methylenedioxyberban, 7,8-dihydroxy-14β-hydroxyalloberban, ethyl 7,8-diethoxy-14β-hydroxyalloberban-13-carboxylate;

15-cyano-14β-hydroxy-7,8-methylenedioxyalloberban,

14β-acetoxy-7,8-methylenedioxyalloberban,

14α-acetoxy-7,8-methylenedioxyalloberban, and ethyl 14β-hydroxy-7,8-methylenedioxyalloberban-13-carboxylate; or a pharmaceutically acceptable acid addition salt thereof.

4. A pharmaceutical composition for treating depression which comprises as active ingredient an antidepressively effective amount of the compound of the Formula (I) as defined in claim 2, or a pharmaceutically acceptable acid addition salt thereof.

5. Methyl 14-beta-hydroxy-7,8-methylenedioxy-alloberban-13-carboxylate or a pharmaceutically acceptable salt thereof as defined in claim 2.

6. Methyl 14-alpha-hydroxy-7,8-methylenedioxyberban-13-carboxylate or a pharmaceutically acceptable salt thereof as defined in claim 2.

7. Ethyl 14-beta-hydroxy-7,8-methylenedioxyalloberban-13-carboxylate or a pharmaceutically acceptable salt thereof as defined in claim 2.

8. 14-beta-hydroxy-7,8-methylenedioxyalloberban or a pharmaceutically acceptable salt thereof as defined in claim 2.

9. 14-alpha-hydroxy-7,8-methylenedioxyalloberban or a pharmaceutically acceptable salt thereof as defined in claim 2.

* * * * *